United States Patent [19]

Beattie et al.

[11] Patent Number: 5,257,530

[45] Date of Patent: Nov. 2, 1993

[54] ACOUSTIC SAND DETECTOR FOR FLUID FLOWSTREAMS

[75] Inventors: Alan G. Beattie, Corrales, N. Mex.; W. Mark Bohon, Frisco, Tex.

[73] Assignees: Atlantic Richfield Company, Los Angeles, Calif.; Sandia Corporation, Albuquerque, N. Mex.

[21] Appl. No.: 788,076

[22] Filed: Nov. 5, 1991

[51] Int. Cl.$^5$ .................... G01F 1/28; G01N 15/07
[52] U.S. Cl. .................. 73/61.75; 73/861.04; 73/861.21; 73/861.73
[58] Field of Search ........... 73/861.04, 861.18, 861.21, 73/861.73, 61.75

[56] References Cited

U.S. PATENT DOCUMENTS

| | | | |
|---|---|---|---|
| 3,816,773 | 6/1974 | Baldwin et al. | 310/8.1 |
| 3,841,144 | 10/1974 | Baldwin . | |
| 3,854,323 | 12/1974 | Hearn et al. . | |
| 4,135,395 | 1/1979 | Sullivan et al. | 73/861.21 |
| 4,240,287 | 12/1980 | Mast et al. . | |
| 4,674,337 | 6/1987 | Jonas . | |

OTHER PUBLICATIONS

Folkestad et al., "Acoustic measurements detect sand in North Sea flow lines" in Oil & Gas Journal, Aug. 27, 1990.

Stuivenwold et al., "Instrumentation for managing sand problem prone fields in society of petroleum", Engineers of AIME, Sep. 1980.

Primary Examiner—Herbert Goldstein
Attorney, Agent, or Firm—Michael E. Martin

[57] ABSTRACT

The particle volume and particle mass production rate of particulate solids entrained in fluid flowstreams such as formation sand or fracture proppant entrained in oil and gas production flowstreams is determined by a system having a metal probe interposed in a flow conduit for transmitting acoustic emissions created by particles impacting the probe to a sensor and signal processing circuit which produces discrete signals related to the impact of each of the particles striking the probe. The volume or mass flow rate of particulates is determined from making an initial particle size distribution and particle energy distribution and comparing the initial energy distribution and/or the initial size distribution with values related to the impact energies of a predetermined number of recorded impacts. The comparison is also used to recalibrate the system to compensate for changes in flow velocity.

16 Claims, 4 Drawing Sheets

ACOUSTIC SAND DETECTOR FOR FLUID FLOWSTREAMS

BACKGROUND OF THE INVENTION

1. Field of the Invention

The present invention pertains to a detector system and method for determining the rate of sand or other particulate solids production or flow in a fluid flowstream, particularly for determining the sand or proppant production rate in an oil or gas well.

2. Background

Various techniques have been developed for determining the presence of particulate solids such as sand in a fluid flowstream. One area of endeavor in which the detection of sand volume or mass flow rate or fracture proppant flow rate is important is in oil and gas production. The monitoring of sand or fracture proppant flow is critical to minimizing excess wear on fluid piping and other flow control components and to control proper production rates from a subterranean reservoir.

U.S. Pat. Nos. 3,841,144 to Baldwin; 3,854,323 to Hearn et al; 4,240,287 to Mast et al; and 4,674,337 to Jonas describe examples known to us representing the prior art in acoustical sand detector devices and methods. An article entitled "Acoustic Measurements Detect Sand in North Sea Flowlines" by Folkestad et al, *Oil and Gas Journal*, Aug. 27, 1990, and a paper entitled "New Instrumentation for Managing Sand Problem Prone Fields" by Stuivenwold et al, SPE No. 9368 by the American Institute of Mining, Metallurgical and Petroleum Engineers, Inc., Sep. 21-24, 1980, also describe acoustic sand detection methods. The Baldwin patent describes an acoustic type detection probe which may be inserted in a fluid flowline and which transmits particle impacts to a piezoelectric type sensor, the output of which is filtered and rectified and compared with a reference signal to provide an output signal indicating the presence of sand in the flowline. The Hearn reference measures sand concentration in a flowline with an acoustic detector wherein the output signal is amplified at two frequencies and resultant signals are combined electronically in such a way that the output signal is a function of sand concentration and nearly independent of fluid flow velocity. The Mast et al patent also describes an acoustic type sand detector wherein the output signal from the detector probe is subjected to a signal pulse height discriminator and pulse counter to determine sand or other particulate solids flow rates. The Jonas patent describes an arrangement of a sand detector probe for a fluid flowline together with noise compensating probes, also attached to the flowline, for subtracting extraneous signal noise from the output signal of the sand detector probe.

The accuracy of the prior art sand detectors described in the above-noted references has not been sufficient to make these devices acceptable commercially in many applications. Accordingly, there has been a continuing need to develop a more accurate sand detector which can distinguish the occurrence of sand or other particulate solids flow in a fluid flowstream and can also accurately determine the flow rate or concentration of sand or particulate solids in the fluid flowstream. The present invention provides a system and method which meets these desiderata.

SUMMARY OF THE INVENTION

The present invention provides an improved sand detector system and method for detecting the presence of and flow rate of sand and other particulate solids in fluid flowstreams. In particular, the present invention provides an improved system and method for determining the presence of and production rate of formation sand and fracture proppant in fluids produced from oil and gas wells.

In accordance with one important aspect of the present invention, a method is provided for determining the particle, volume or mass production rate of sand or similar particulate solids in a fluid flowstream wherein individual particles are detected and the actual rate of particles can be determined from a particle size distribution which is predetermined for the source of particulate solids in the flowstream.

In accordance with another important aspect of the present invention, a method for determining the volume or mass flow rate of sand or other particulate solids in a fluid flowstream is provided wherein a distribution of measured particle impact energies and a distribution of particle impact energies based on a predetermined particle size or volume are compared to determine the rate of solids particles in the flowstream.

In accordance with yet another important aspect of the present invention, a system is provided which includes a detector probe which converts a mechanical vibration of the probe due to impacting of a particle against the probe into an electrical signal which is proportional to the impact energy of the particle. Each individual particle impact energy is converted into an equivalent particle mass and the particle masses are summed and converted into a particle mass or volume production rate.

In accordance with still a further aspect of the present invention, an improved particulate solids detection system is provided which is operable to determine particle mass or volume production rates in a fluid flowstream. The system utilizes a metal probe extending into the conduit for the flowstream and intersecting the fluid flowstream in such a way that acoustic impulses are created by particles striking the probe and are transmitted through the probe to a detector located on the outside of the conduit. A preamplifier is provided for amplifying the signals and transmitting them to a signal processing circuit which provides signals for a calibrating method which may be carried out by a digital computer.

The above-mentioned advantages and superior features together with other important aspects of the present invention will be further appreciated by those skilled in the art upon reading the description which follows in conjunction with the drawing.

DESCRIPTION OF PREFERRED EMBODIMENTS

In the description which follows, like elements are marked throughout the specification and drawing with the same reference numerals, respectively. The drawing figures illustrating structure are not necessarily to scale.

Figure 1:
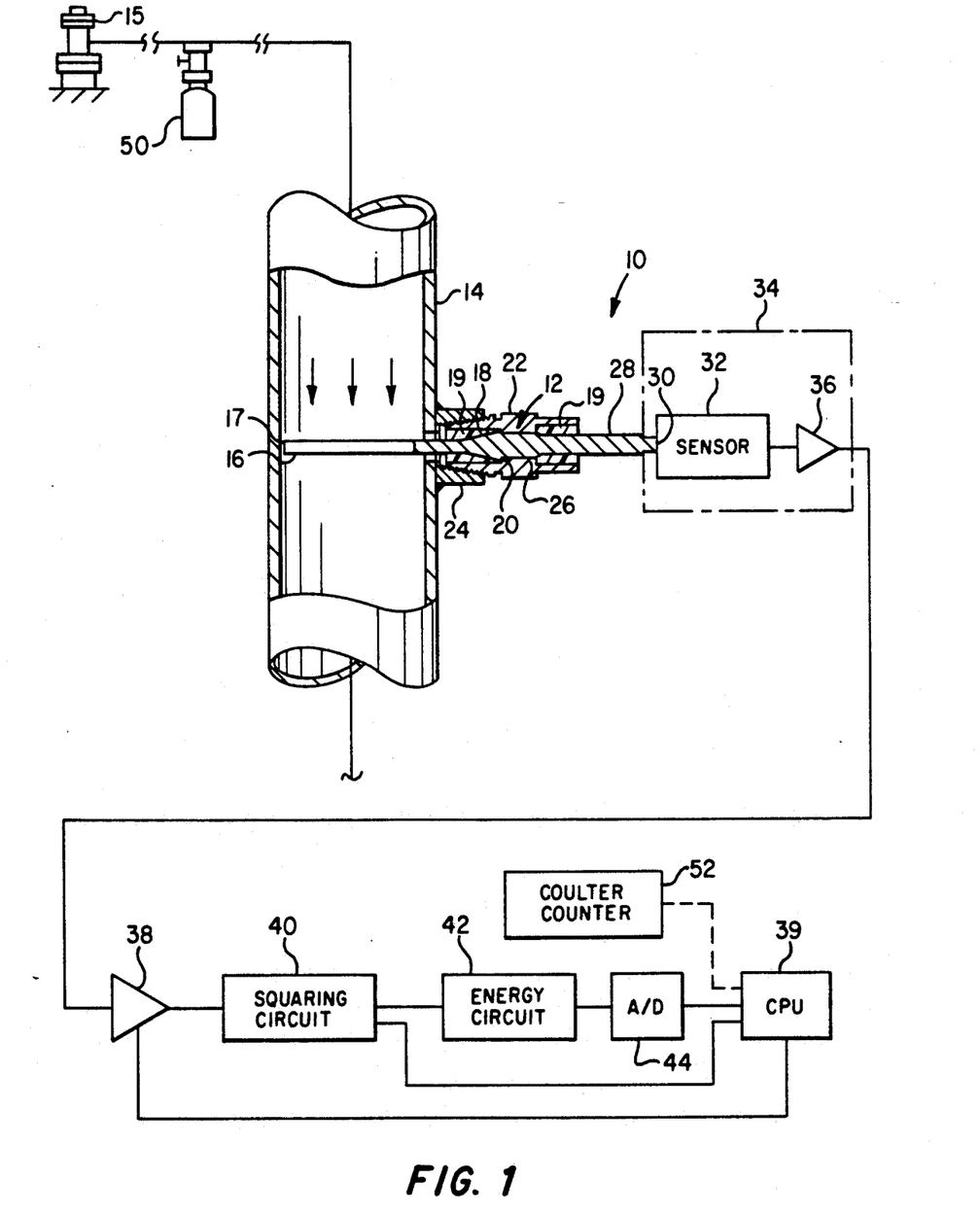
FIG. 1 is a schematic diagram of the improved sand detection system of the present invention.

Referring to FIG. 1, the basic elements of an improved sand detector system 10 are illustrated. The detector system 10 is characterized by a probe comprising a metal cylindrical rod, generally designated by the numeral 12, which is adapted to be supported on and extend within a section of pipe or conduit 14 which preferably extends generally vertically and is operable to conduct mixed phase fluids such as gas, oil and water from a producing oil well 15. Typically, the flow from a producing oil or gas well may include mixtures of gas, water and crude oil or other hydrocarbon fluids and particulate solids such as formation sand. In some instances, when a well is producing fluids from a formation which has been hydraulically fractured, proppant material comprising graded sand or the like may also be carried with the produced fluid as it flows to the surface. The production of sand and/or fracture proppant from a producing well should be monitored, and controlled in many instances, to prevent damage to the producing system, damage to the formation, or possible plugging of the well itself.

The probe 12 includes a generally cylindrical cross-section detector portion 16 which may or may not extend substantially across the inside diameter of the conduit 14 and maintain at least a small (approximately 0.12 inches) clearance at its distal end 17 with respect to the inside wall of the conduit. The probe 12 may include a section 18 which forms a transverse shoulder 20 butted against a cooperating shoulder formed on a support fitting 22 which is suitably threaded to provide for supporting the probe 12 to extend into the conduit 14 as provided by a suitably internally-threaded boss 24. Suitable acoustic damping compound 19 should be disposed around the probe at the areas indicated in FIG. 1. Moreover, it has been determined that the threaded connection between the fitting 22 and the boss 24, using conventional pipe threads, tends to attenuate the transmission of high frequency acoustic signals (in the range of interest) from the conduit 14 to the probe 12. A second portion of the probe 12, characterized by a section 26, is preferably interference fitted into a cooperating bore in the fitting 22. The probe 12 further includes a shaft portion 28 which is delimited by a transverse end face 30 which is engaged with a suitable acoustic vibration sensor 32. By way of example, the probe may comprise a rod of 316L stainless steel and the diameter of the detector portion 16 being approximately 0.50 inches while the diameter of the section 28 is approximately 0.375 inches. The geometry of the exemplary probe 12 is also such as to give a maximum length of impact signals resulting from impacting of solid particles against the portion 16 of between 0.2 and 0.4 milliseconds.

The sensor 32 is preferably disposed in a suitable enclosure 34 together with a preamplifier 36. The sensor 32 preferably comprises a piezoelectric element which is mounted on a small plate which is spring biased against the surface 30. An acoustic emission sensor such as a Micro Sensor 100 from Physical Acoustic Corporation could be used instead of the piezoelectric element. Acoustic coupling may be made with vacuum grease or the like. The sensor 32 preferably has a maximum sensitivity in the range of 300 KHz to 800 KHz. Solid particles impacting the detector portion 16 will result in vibratory displacement of the section 28 to oscillate the sensor 32. This oscillatory displacement is converted into a variable voltage signal which is a function of displacement and is related to the energy of impact of a solid particle against the detector portion 16.

In a preferred embodiment of the system 10, the preamplifier 36 is designed for 20dB gain at the band pass range of 300 KHz to 800 KHz. The enclosure 34 may be a commercially available explosion-proof box which is configured to be suitably detachably mounted to the probe section 28 by a suitable fitting, not shown, which will allow easy replacement of the probe 12 or the sensor 32 and the preamplifier 36.

An output voltage signal from the preamplifier 36 is conducted to a variable gain amplifier 38 which preferably has a 0dB to 42dB gain in six steps and also capable of handling signals in a 300 KHz to 800 KHz band pass. By way of example, the amplifier 38 may be set for 0dB gain for detection of relatively high-mass particles such as fracture proppant or the full 42dB gain for the detection of relatively fine sand. The output signal from the amplifier 38 is transmitted to a signal voltage squaring circuit 40 which also has suitable filters including a 10 KHz low-pass filter. Part of the output signal from the squaring circuit 40 is transmitted through a 1 Hz low-pass filter to give an average signal level. This output signal is multiplied by 1.25, for example, to obtain a threshold voltage for particle detection. The other part of the 10 KHz filtered signal is transmitted through a circuit 42 which measures the area under the voltage squared versus time curve which is proportional to the acoustic impact energy of the particles striking the probe 12.

Figure 3:
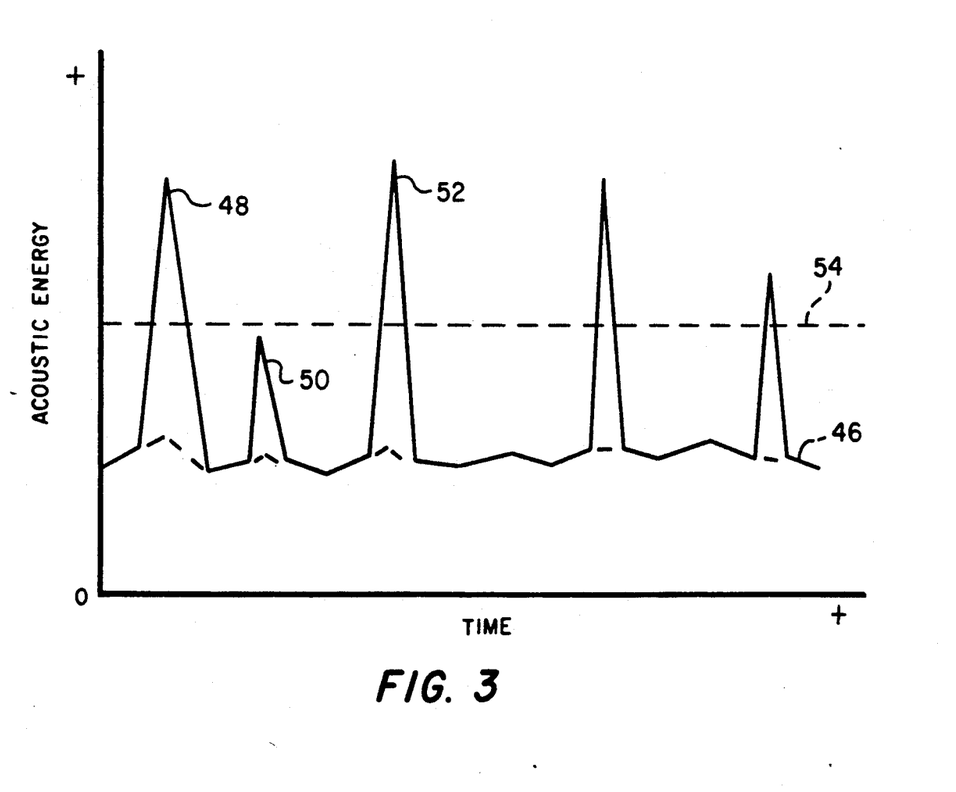
FIG. 3, is a diagram illustrating the relationship of the acoustic energy sensed by the probe as a function of time.

Referring briefly to FIG. 3, there is illustrated a plot of acoustic energy versus time which is essentially the output of circuit 42. In other words, the input signal to the circuit 40 is a fluctuating voltage as determined by the vibration of the sensor 32 and the output of the circuit 42 is of the characteristic indicated by the curve of FIG. 3. The signal level indicated by the line 46 in FIG. 3 is generally categorized as background noise which may result from fluid flow turbulence and gas bubbles in the fluid stream, for example. The sharp peaks 48, 50, 52 and so on are those created by the impacting of particles against the probe detector portion 16. In order to record only those impacts which are significant, a threshold level of signal as indicated by the line 54 is prescribed for the circuit 42 so that any time the threshold voltage squared signal from the circuit 40 exceeds the level indicated by the line 54, the circuit is activated to measure the area under the peaks 48, 52, for example. The measured values of the area under the peaks 48 and 52 and so on are transmitted to the CPU 39.

As mentioned earlier, the probe 12 is preferably designed to generate signals at a rate of up to 2000 per second. Higher rates could be estimated from the signal area above the threshold signal. However, it is believed that a flow rate of 2000 particles per second impacting the detector portion 16 is a rate considerably higher than would be seen in normal operation of the system 10. Accordingly, the CPU 39 may be adapted to read the signal from the circuits 40 and 42 by way of an A to D converter 44 at a rate of up to 2000 times a second and transfer any signals above the threshold 54, FIG. 3, into the CPU 39. Periodically, every 10 seconds for example, the CPU 39 may be operated to count the number of signals above the threshold value and display an upgraded particle rate.

The particle signal rates may be multiplied by the ratio of the cross-sectional area of the conduit 14 to the cross-sectional area of the cylindrical detector portion 16 to obtain the particle rates flowing through the conduit. The CPU 39 may also be programmed to add a small correction value to each impact energy based on the threshold value and each impact energy may also be multiplied by a number calculated by one embodiment of a calibration method to be described herein which will convert the impact energy into an equivalent particle mass. The particle masses may then be summed and converted into a mass production rate for the well 16, such as in units of pounds or kilograms per hour or per day.

The signals generated by the circuits 40 and 42 are preferably stored in ring buffers, not shown, 2000 words long. These ring buffers, once they are filled, will always contain the last 2000 input signals. There may be a buffer for multiple channels for the CPU 39 so that more than one well may be monitored at the same time, although only one well is shown for the system 10. In this way a current set of energies for calibration will always be available. The acoustic impact energies may also be checked during the calibration procedure to be described to determine if many of the energies fall outside of the range of the energy-measuring circuit. If such is the case, the gain of the amplifier 38 is adjusted up or down in 6 dB increments as necessary.

In order to determine the masses of the particles which generate impact energies or signals such as the signals 48 and 52 in FIG. 3, a unique calibration or matching procedure is carried out in accordance with the present invention. This procedure is based on the premise that the distribution of energy signals will correspond to the distribution of measured particle volumes and that similar distributions will maintain the same shape when plotted on logarithmic scales, for example, even if they have quite different orders of magnitude, at least on the energy axis of the scale. For example, a distribution of measured particle sizes, converted to particle volumes or masses, if desired, and a distribution of particle acoustic impact energies can be compared if the axes of both distributions are truly proportional to the particle mass. Particles impacting normal to a flat surface will generate impact energies proportional to their kinetic energy. If the velocity of all particles is constant, the impact energy will be proportional to the mass of each individual particle. In a conduit where there is a relatively steady flow, even when it is a two-phase flow, most of the particles should have approximately the same velocity, so the assumption is valid for the methodology described herein and one can determine the mass of a particle from its acoustic impact or pulse energy. The shape of the particle and the dynamics of the impact will have some effect but this should be insignificant for measurement of relatively hard particles of the same material, that is sand from a single formation or proppant material which has been predetermined to be of known characteristics.

The probe 12 is designed to have a cylindrical detector portion 16 so that orientation of the probe in the conduit is not a source of error. However, particles striking a cylindrical cross-section rod, see FIG. 2, will generate acoustic impact energies dependent on the angle between the particle velocity vector and the radius of the rod. An approximation of the impact energy for identical particles should vary as the square of the cosine of the angle $\theta$, FIG. 2. The angle $\theta$ is that which is formed by a velocity vector, such as line 49 in FIG. 2, and a line normal to the rod surface at the point of impact. Accordingly, a statistical estimate of the probability of a particle generating an acoustical pulse energy less than that of a head-on collision can be made. A transfer function, $H(i)$ may be determined for the cylindrical detector portion 16 which gives the probability of the acoustic energy generated by the particle impact being equal to or lower than the energy that would be generated by impact with a flat plate. These probabilities can also be determined as described below.

Figure 2:
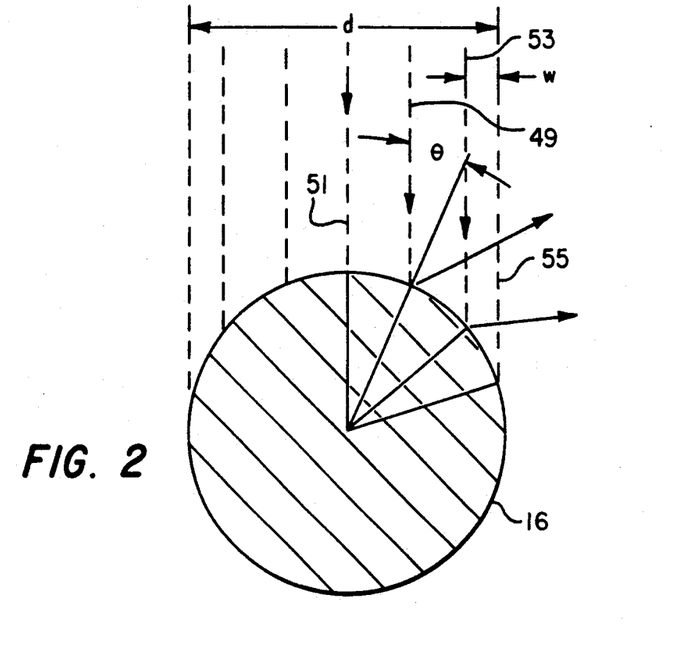
FIG. 2 is a diagram illustrating certain relationships used in determining the probability of a particle hitting a cylindrical cross-section probe.

Referring to FIG. 2, a selected number of widths w corresponding to a range of values of the angle $\theta$ may be determined for the cross-sectional profile of the detector portion 16. These widths will vary as a portion of the total width or diameter d of the cross-sectional profile of the detector portion 16. Moreover, for a given particle size there is a probability that, at an assumed velocity, such a particle will produce an energy value which varies as the width w as a portion of the total diameter d and the number of particles of that size. For example, a particle of a certain size (diameter) will produce a higher acoustic energy if it impacts the detector portion 16 along line 51 than if it impacts along line 53 or anywhere in the range of angles between the line 53 and the line 55, for example. Secondly, a particle of a larger diameter may produce the same impact energy as the first mentioned particle did along the line 53 if the larger particle impacts the detector portion 16 along line 55, for example. The probability of a given particle size producing a given impact energy value may be determined from the ratio of each of the widths w of the selected number of widths to the diameter d.

In accordance with the method of the present invention, the particle size distribution is taken by using a particle size analyzer which will analyze the particle size distribution of a sample of particulate solids produced with the flowstream in the conduit 14. For example, a sample of the particles being conducted with the flowstream flowing through the conduit 14 may be obtained from a suitable sampling container 50. Other devices, such as slug catchers, and other methods may be used for retaining at least samples of sand or other particulate solids being conducted through a conduit.

The collected particles may be measured by a Coulter particle size distribution analyzer such as a Model LS100, commercially available from Coulter Industrial Company of Elmhurst, Ill. The particle size distribution from the Coulter counter 52, FIG. 1, from the sample taken by the sampling container 50 may be input to the CPU 39 as a reference. Since the Coulter counter 52 counts the particles by size (diameter) distribution, the output information from the Coulter counter 52 may also be easily converted into a particle volume distribution and, assuming a constant density, a particle mass distribution.

Figure 4:
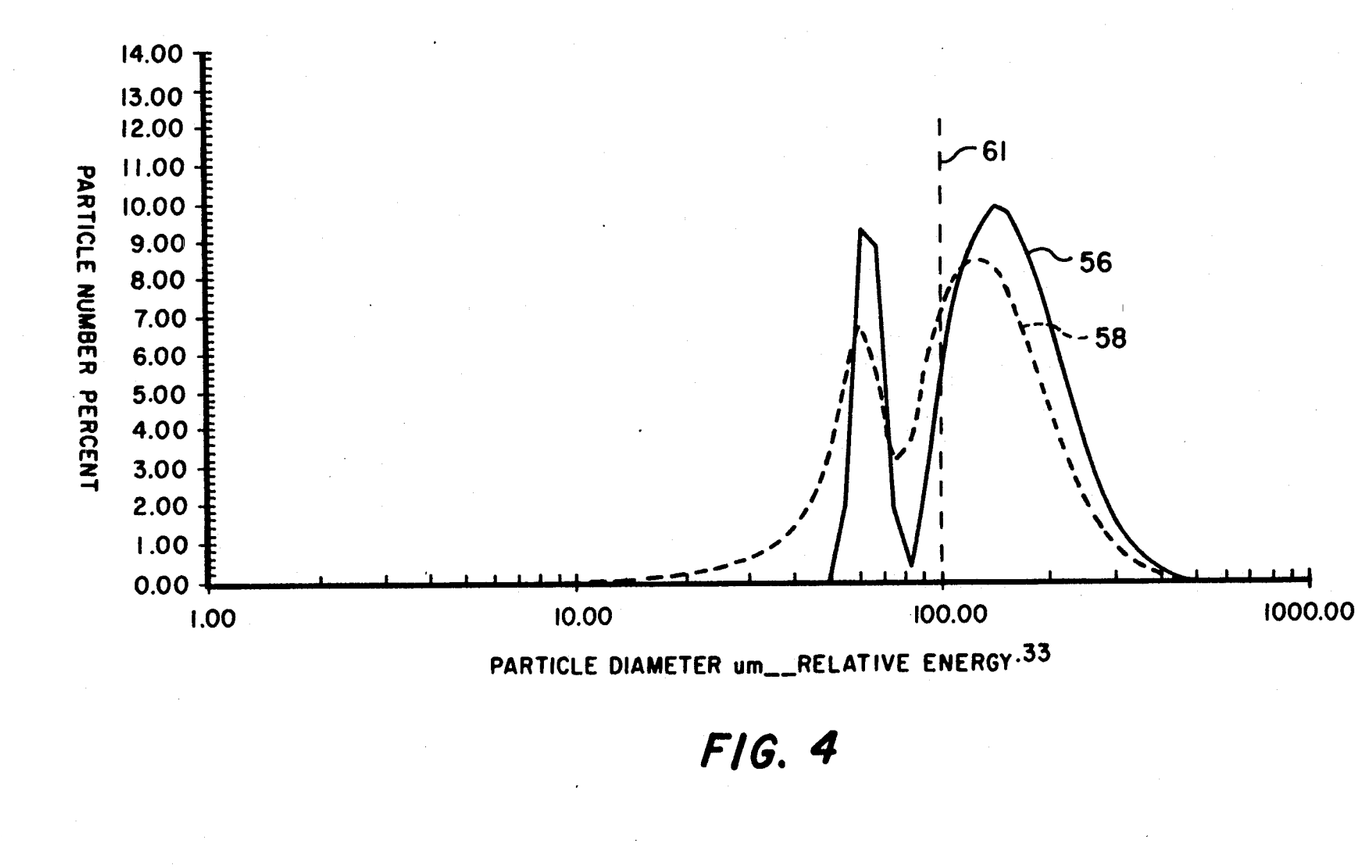
FIG. 4 is a diagram showing the relationship between the distribution of particles and the distribution of particle impact energies.

FIG. 4 illustrates the relationship between one particular particle size distribution (particle diameter in microns), as indicated by the solid line 56, and the corresponding relative acoustic energy distribution generated by the particles as indicated by the line 58, both as a function of the percentage of particle numbers. The abscissa of the diagram of FIG. 4 is a logarithmic scale. As a practical approach, the spacing of the logarithmic scales is based on the spacing or width of the incremental particle size ranges or "bins" of the Coulter counter 52. The width of the bins of the above-mentioned Coulter counter, based on particle size, is 0.0458 and the width of the bins of volume or energy values is 0.1375 since both are proportional to the diameter cubed. The output from the Coulter counter 52 is converted into particle mass distribution based on the particle diameter distribution analyzed by the counter and the particle density.

Accordingly, the CPU 39 may be programmed to take a current set of particle impact energies from the aforementioned buffer, calculate the log of each particle energy, find the maximum and minimum of the logs of the energies and divide the span in log energy into bins having a width of 0.1375 based on the width of the bins of the log volumes from the Coulter counter 52. Arrays, E(j), may be created containing the number of particles in each bin. The Coulter analyzer data, that is the volume of particles per bin, and the average dimension of a bin opening may then be placed in an array, D(i), consisting of the relative number of particles in each bin. The number, n1, of the largest bin with more than one particle in the major part of the distribution curve is determined. A small distribution peak containing a few larger particles should probably be ignored.

An array is then calculated as follows:

$$A(n1 + 1 - j) = \sum_{i=1}^{j} (H(n2 + 1 - i)*D(n1 + i - j))$$

for as many values of j as there are entries in D(i). This procedure forms the distribution of impact energies that one would expect from the distribution D(i) hitting a cylindrical cross-section rod.

An array is then formed comprising:

$$F(i) = D(i)/A(i)$$

The array D(i) is illustrated by the line 56 in FIG. 4 and the array A(i) is illustrated by the line 58. Because D(i) and A(i) are essentially histograms the function F(i) will not be smooth but may be converted to a continuous function $f(\log(U_i))$, by various mathematical procedures, such as forming a sum of orthogonal functions, such that:

$$c_i = f(\log(U_i))$$

where $c_i$ is the statistical correction factor for the volume of a particle with shifted energy $U_i$ and f( ) is the sum of orthogonal functions.

To shift the energy distribution to a volume distribution, the peaks in the particle energy distribution, E(j), and the modified sand volume distribution A(i) are determined. The difference in the position of the peaks on the abscissa (the log scales) is added to the energy scales so that the curves are now superimposed. If this difference is Con, then the log of the particle volume is $$\log(U_i) = \log(E_i) + Con$$

the particle mass is now $$M_i = c_i * U_i * \rho$$

where $\rho$ is the particle density.

One more correction should be made. The percent volume is calculated as a function of each bin with zero as the first bin above the highest occupied bin and 100 as the lowest occupied bin. By counting the number of occupied bins in the energy distribution function and subtracting from the number of the highest occupied bin in the percent volume function, the percent volume that the measured range of acoustic energy samples may be found. Dividing the particle volume by this percent volume then corrects for the volume of particles which are too small to trigger the energy-measuring threshold. Such corrections appear to be small for the recorded data from oil and gas wells and the sand particle volume distributions tested to date, usually under ten percent (10%).

The CPU 39 will calculate the array E(j) from the correct 2000 entries in the ring buffer of the CPU periodically, once a minute for example. If the shape or position of the distribution E(j) has changed from the previous calculation, the CPU will then recalculate Con, thus recalibrating the system. This will correct for any changes in flow velocity which has occurred in the previous time period. At the same time the measured particle energies will be checked to determine if they fall within the range of the energy measuring circuit 42. If a change in flow velocity has caused too many particle energies to be out of range of the circuit 42, the CPU 39 will change the gain of amplifier 38 until the particle energies again lie within the range of circuit 42. In this way, the system 10 is self-calibrating and self-correcting for changes in the flow velocity.

The aforementioned methodology may be carried out in a program which will run automatically after the system 10 is started and a particle size distribution curve is selected or created by the Coulter counter 52. The program may display the actual rate of particles per minute hitting the probe 12 as well as the estimated particles per minute in the conduit 14. A program may also display the estimated rate of particle production in pounds per day and/or cubic feet per day. Instantaneous rates may be recalculated periodically, such as every ten (10) seconds.

The CPU 39 may also be programmed to go into the particle counting mode any time the system 10 is turned on and may be operated to determine if it is counting sand or proppant material, for example. The gain of the amplifier 38 will then be set accordingly. A library of particle size distributions may be pre-programmed and selected among the possible size ranges. This may be done for selected proppant sizes and sand distributions likely to be encountered in a particular flowstream.

An alternate calibration method according to the present invention may be carried out also by collecting a sample of produced solids from the well 15 with the collector container 50 and analyzing the particle size distribution. As with the previous described method, particle sizes may be quantized in the bins of the Coulter counter 52. The number percent distribution in FIG. 4 is an example as indicated by the curve 56.

As previously discussed, particles impacting a flat surface will generate impact energies proportional to their kinetic energy. Assuming the velocity is constant, the impact energy will be proportional to the mass of each individual particle, that is proportional to the diameter cubed. If the particles impact the round or cylindrical detector portion 16, the impact energies are proportional to the square of the cosine of angle $\theta$ as well as the particle mass. The probability that a particle of a given diameter produces an impact of a given energy may be calculated as indicated hereinabove.

The distribution of impact energies on a cylindrical probe will be produced by random collisions with particles of a specific particle size distribution which may be calculated by multiplying the probability that a given size particle will produce a given impact energy by the number percent of that particle size and summing over all particle sizes in the specified distribution. The energy distribution shown in FIG. 4, as indicated by curve 58, is one such distribution. The energy distribution in FIG. 4 corresponds to a particular particle velocity. At other velocities, the distribution will be shifted but the shape of the curve 58 will remain the same. The shape of the logarithmic energy distribution produced by a particular particle size distribution is therefore invariant with changes in flow velocity. Moreover, in operation, the energy distribution curve 58 will shift left and right, viewing FIG. 4, as the flow velocity changes. Background noise and the threshold of detection will also shift. The system 10 may be adapted to detect a change in the background noise and threshold and at times the threshold of detection will fall within the main body of the expected energy distribution as indicated, for example, by line 61 in FIG. 4. That portion below the threshold will not be detected.

Figure 5:
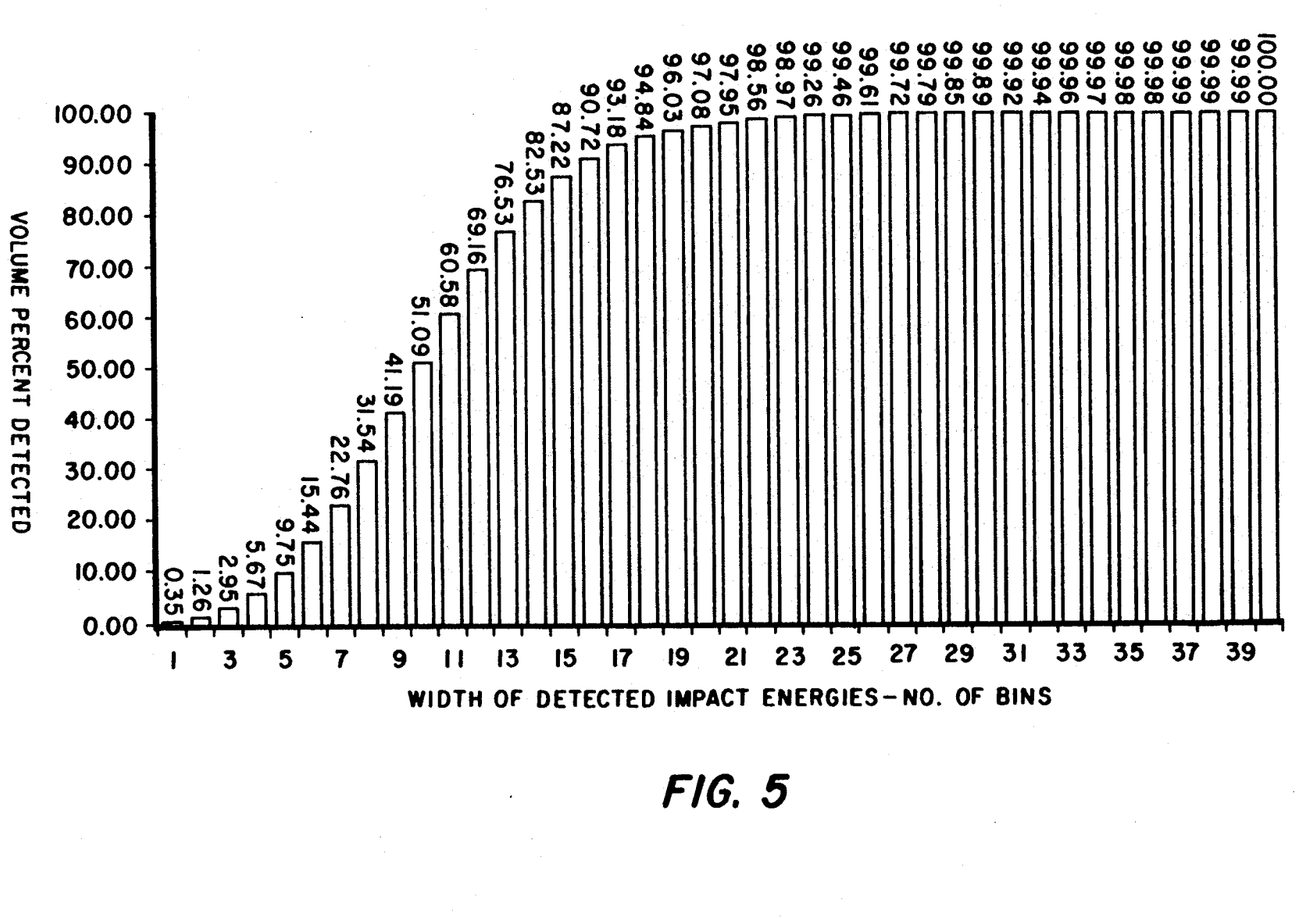
FIG. 5 is a diagram of the percent volume of sand detected compared with the number of ranges of magnitude of detected particle impact energies.

However, in the alternate method the energy distribution is divided into discrete bins or energy value ranges, preferably based on the range or width of the bins of the Coulter counter 52, or 0.1375. Beginning with the highest energy bin (1) and working to the lowest, the cumulative volume percent of the original particle size distribution that contributed to that energy bin may be calculated by multiplying the probability that a given size particle will produce a given impact energy by the volume percent represented by that particle size, summing over all the particle diameters, and summing over the energy bins from the highest energy bin to the threshold energy bin. FIG. 5 is a diagram showing the cumulative volume percent versus the number of impact energy bins detected for the particle diameter distribution and relative energy distribution of FIG. 4.

The characteristics of the diagrams of FIGS. 4 and 5 are determined prior to operation of the system 10 for a particular operating condition but based on the particle size distribution input provided from the Coulter counter 52 to the CPU 39. After commencing operation of the system 10 an array of impact energies may be recorded, namely the 2000 stored energies retrieved from the aforementioned buffer. The logarithms of the maximum and minimum energies may be subtracted from the total and the remainder divided by 0.1375 (the energy bin width) to obtain an integer value. This is the number of energy bins that the 2000 impact energies are distributed over. The diagram of FIG. 4 is entered with this value and the resultant volume percent of the total sand volume detected is obtained from FIG. 5. Since the initial distribution of particle volume of 2000 particles is known, this volume divided by the percent detected from FIG. 5 (multiplied by the ratio of the conduit 14 cross-sectional area to the cross-sectional area of the probe section 16) renders the total volume of sand produced during the period that the 2000 impacts were recorded. This volume divided by the duration over which the 2000 impacts were recorded is the volumetric sand production rate.

Although a preferred embodiment of a system in accordance with the present invention has been described and although two preferred embodiments of a method according to the present invention have also been described, those skilled in the art will recognize that various substitutions and modifications may be made to the invention without departing from the scope and spirit of the appended claims.

What is claimed is:

1. A system for determining at least one of the particle production rate, particle volume production rate, and particle mass production rate of particulate solids entrained in a fluid flowstream flowing through a conduit and the like, said system comprising:

impact-receiving means intersecting said flowstream and adapted to be impacted by at least some of the entrained particles in said fluid flowstream and for transmitting acoustic energy generated by the impacts of the particles to sensor means;

sensor means connected to said impact-receiving means for converting mechanical displacement of said impact-receiving means to an electrical signal;

amplifier means for amplifying the magnitude of said electrical signal; and circuit means for converting said electrical signal for each impact to a signal which is proportional to the energy imparted to said impact-receiving means by each particle impacting said impact-receiving means over a predetermined period of time, said circuit means including a variable gain amplifier for transmitting voltage signals in a frequency range of at least 300 KHz to 800 KHz ban pass and means for multiplying the voltage signal output from said variable gain amplifier times itself to provide a voltage squared output signal.

2. The system set forth in claim 1 wherein:

said circuit means includes means for measuring the area of the voltage squared signal versus time to provide which is proportional to the acoustic impact energy of particles impacting said impact-receiving means.

3. The system set forth in claim 2 wherein:

said circuit means includes means for ignoring voltage squared signals below a threshold signal magnitude to minimize the transmission of signals which are insignificant.

4. A method for determining at least one of the particle production rate, particle volume production rate and particle mass production rate of particulate solids entrained in a fluid flowstream comprising the steps of:

providing impact-receiving means for being interposed in said fluid flowstream to be impacted by at least a portion of the particles flowing with said fluid flowstream, said impact-receiving means including means for converting acoustic signals generated by the impact of each of said particles to respective energy signals proportional to the impact energies of said particles;

determining the particle size distribution of the particles entrained in said fluid flowstream;

recording a selected number of energy signals proportional to the impact energies of said particles, respectively;

comparing the distribution of energy signals proportional to the impact energies of said particles, respectively, with said particle size distribution to determine said at least one of particle production rate, volume production rate and mass production rate of the particulate solids entrained in said flowstream.

5. The method set forth in claim 4 including the steps of:

determining the logarithms of each recorded energy signal and dividing the span of the values of logarithmic energy signals into ranges related to the ranges of the predetermined particle size distribution to provide arrays containing the number of particles in each range.

6. The method set forth in claim 5 wherein:

said impact-receiving means comprises a cylindrical cross-section member and said method includes the step of determining the probability of the energy signal generated by said impact-receiving means being equal to or lower than the energy signal that would be generated by impact with a flat plate and calculating an array A(i) of particle volume distribution:

$$A(n1 + 1 - j) = \sum_{i=1}^{j} (H(n2 + 1 - i) * D(n1 + i - j))$$

for as many values of j as there are entries in D(i) wherein D(i) is an array consisting of the relative number of particles in each particle size distribution range, n1 is the number of the largest range with more than one particle to form the distribution of impact energies impacting said member and H(i) is a transfer function which gives the probability of the impact energy of a particle impacting said member being lower than the energy generated by impacting a flat plate.

7. The method set forth in claim 6 including the steps of:

determining an array:

$$F(i) = D(i)/A(i)$$

and converting the array F(i) to a continuous function $f(\log(U_i))$ such that:

$$c_i = f(\log(U_i))$$

wherein $c_i$ is the statistical correction factor for the volume of a particle with shifted energy $U_i$ and $f(\ )$ is the sum of said orthogonal functions.

8. The method set forth in claim 7 including the step of:

comparing the energy distribution to a volume distribution to find the difference between peaks in the particle energy distribution and the particle volume distribution; and adding the difference in the position of the peaks so that the particle size distribution and the energy distribution of the particles are superimposed on a logarithmic scale.

9. The method set forth in claim 8 including the step of:

determining the difference in the position of the peaks on the logarithmic scale, Con, and determining the logarithm of the particle volume from the relationships:

$$\log(U_i) = \log(E_i) + Con$$

and calculating the particle mass from the relationship:

$$M_i = c_i * U_i * \rho$$

wherein $M_i$ is the particle mass and $\rho$ is the particle density.

10. The method set forth in claim 9 including the step of:

calculating the percent volume as a function of each range of volume with zero as the first range above the highest occupied range and 100 as the lowest occupied range by counting the number of occupied ranges in the energy distribution function and subtracting from the number of the highest occupied range in the percent volume function to determined the percent volume that the measured range of acoustic energy is a sample, and dividing the particle volume by the percent volume to correct for the volume of particles which are too small to generate signals related to the impact energy of particles impacting said impact-receiving means.

11. The method set forth in claim 4 including the step of:

determining a distribution of energy values proportional to the particle impact energies based on the predetermined particle size distribution.

12. The method set forth in claim 11 including the steps of:

dividing the energy value distribution into discrete ranges of energy values; and for each energy value range determining the cumulative volume percent of the original particle size distribution that contributed to that energy value range to determine the cumulative volume percent of particles as a function of the number of energy value ranges.

13. The method set forth in claim 12 including the step of:

multiplying the probability that a given size particle will produce a given impact energy against a cylindrical cross-section impact-receiving means by the volume percent represented by that particle size.

14. The method set forth in claim 12 including the step of:

determining an array of the recorded energy signals having the same range as the range of the predetermined energy values, determining the number of ranges that the recorded energy signals are distributed over and comparing the number of ranges of recorded energy signals with the cumulative volume percent to determine the percent of the total particle volume that the recorded energy signals represent.

15. The method set forth in claims 10 or 14 including the step of:

multiplying the ratio of the conduit cross-sectional area to the cross-sectional area of the impact-receiving means to determine the total volume of particles produced in the flowstream during the period that the impact-energy signals were recorded.

16. The method set forth in claim 4 including the step of:

redetermining the particle size distribution from time to time and determining the difference in the peaks of the particle size distribution and the particle energy distribution on a logarithmic scale to compensate for changes in flow velocity of said flowstream.

* * * * *